United States Patent
Saban et al.

(10) Patent No.: US 7,947,825 B2
(45) Date of Patent: May 24, 2011

(54) PROCESS FOR MAKING TITANYL PHTHALOCYANINE

(75) Inventors: Marko D. Saban, Toronto (CA); George Liebermann, Mississauga (CA); Roger E. Gaynor, Oakville (CA); Sandra Gardner, Oakville (CA); Cuong Vong, Hamilton (CA); Evelyn Juandi, Toronto (CA)

(73) Assignee: Xerox Corporation, Norwalk, CT (US)

( * ) Notice: Subject to any disclaimer, the term of this patent is extended or adjusted under 35 U.S.C. 154(b) by 1136 days.

(21) Appl. No.: 11/706,892

(22) Filed: Feb. 13, 2007

(65) Prior Publication Data

US 2008/0194814 A1   Aug. 14, 2008

(51) Int. Cl.
*C07B 47/00* (2006.01)
*C07D 487/22* (2006.01)
(52) U.S. Cl. ...................................................... 540/145
(58) Field of Classification Search .................. 540/145
See application file for complete search history.

(56) References Cited

U.S. PATENT DOCUMENTS

| | | | |
|---|---|---|---|
| 4,664,997 A | 5/1987 | Suzuki et al. |
| 4,728,592 A | 3/1988 | Ohaku et al. |
| 4,898,799 A | 2/1990 | Fujimaki et al. |
| 5,132,197 A | 7/1992 | Iuchi et al. |
| 5,164,493 A | 11/1992 | Mayo et al. |
| 5,189,155 A | 2/1993 | Mayo et al. |
| 5,189,156 A | 2/1993 | Mayo et al. |
| H1474 H | 8/1995 | Martin et al. |

*Primary Examiner* — Paul V. Ward
(74) *Attorney, Agent, or Firm* — Pillsbury Winthrop Shaw Pittman LLP

(57) ABSTRACT

Processes for making organic pigments useful in imaging members, specifically for pigments that after further polymorphic conversion may be used in a charge generating layer of an imaging member. More specifically, there are described processes for producing titanyl phthalocyanine (TiOPc) in high yields using tetrahydronaphthalene as reaction solvent, such as TiOPc Type I. This pigment can be successfully converted to a high sensitivity crystal form useful as charge generating pigment in an imaging member.

9 Claims, 2 Drawing Sheets

PROCESS FOR MAKING TITANYL PHTHALOCYANINE

TECHNICAL FIELD

The present disclosure relates generally to organic photosensitive pigments used in imaging members, such as layered photoreceptor devices, and novel processes for producing the pigments. The imaging members can-be used in electrophotographic, electrostatographic, xerographic and like devices, including printers, copiers, scanners, facsimiles, and including digital, image-on-image, and like devices. More specifically, the present embodiments relate to processes for producing titanyl phthalocyanine (TiOPc) in high yields, using tetrahydronaphthalene as solvent, which does not present toxicity or safety issues.

BACKGROUND

Electrophotographic imaging members, e.g., photoreceptors, typically include a photoconductive layer formed on an electrically conductive substrate. The photoconductive layer is an insulator in the substantial absence of light so that electric charges are retained on its surface. Upon exposure to light, charge is generated by the photoactive pigment, and under applied field charge moves through the photoreceptor and the charge is dissipated.

In electrophotography, also known as xerography, electrophotographic imaging or electrostatographic imaging, the surface of an electrophotographic plate, drum, belt or the like (imaging member or photoreceptor) containing a photoconductive insulating layer on a conductive layer is first uniformly electrostatically charged. The imaging member is then exposed to a pattern of activating electromagnetic radiation, such as light. Charge generated by the photoactive pigment move under the force of the applied field. The movement of the charge through the photoreceptor selectively dissipates the charge on the illuminated areas of the photoconductive insulating layer while leaving behind an electrostatic latent image. This electrostatic latent image may then be developed to form a visible image by depositing oppositely charged particles on the surface of the photoconductive insulating layer. The resulting visible image may then be transferred from the imaging member directly or indirectly (such as by a transfer or other member) to a print substrate, such as transparency or paper. The imaging process may be repeated many times with reusable imaging members.

An electrophotographic imaging member may be provided in a number of forms. For example, the imaging member may be a homogeneous layer of a single material such as vitreous selenium or it may be a composite layer containing a photoconductor and another material. In addition, the imaging member may be layered. These layers can be in any order, and sometimes can be combined in a single or mixed layer.

Typical multilayered photoreceptors have at least two layers, and may include a substrate, a conductive layer, an optional charge blocking layer, an optional adhesive layer, a photogenerating layer (sometimes referred to as, and used herein interchangeably, a "charge generation layer," "charge generating layer," or "charge generator layer"), a charge transport layer, an optional overcoating layer and, in some belt embodiments, an anticurl backing layer. In the multilayer configuration, the active layers of the photoreceptor are the charge generating layer (CGL) and the charge transport layer (CTL).

As more advanced, higher speed electrophotographic copiers, duplicators and printers were developed, however, degradation of image quality was encountered during extended cycling. The complex, highly sophisticated duplicating and printing systems operating at very high speeds have placed stringent requirements, including narrow operating limits, on the imaging members. Thus, photoreceptor materials are required to exhibit, not only efficient charge generation and charge transport properties, but also structural integrity and robustness so as to withstand mechanical abrasion during image development cycles.

Organic photosensitive pigments are widely used as photoactive components in charge generating layers. One such pigment used in the CGL in electrophotographic devices is titanyl phthalocyanines (TiOPc). As explained in U.S. Pat. No. 5,164,493, which is hereby incorporated by reference in its entirety, polymorphism or the ability to form distinct solid state forms is well known in phthalocyanines. For example, there are four main crystal forms of TiOPc known, Types I, II, III and IV. TiOPc Type IV offers many attractive features as a photosensitive pigment, but is especially of interest because of its high efficiency of charge generation. For example, TiOPc Type IV is a faster photosensitive pigment than hydroxygallium phthalocyanine (HOGaPc). The Type IV polymorph is made by a polymorphic conversion from the Type I polymorph, as disclosed, for example, in U.S. Pat. No. 5,189,155, which is hereby incorporated by reference in its entirety. General processes for making the Type I polymorph are disclosed in U.S. Pat. Nos. 4,664,997, 4,728,592, 4,898, 799, 5,132,197, 5,189,155, 5,189,156 and H1,474, which are hereby incorporated by reference in their entirety. Many conventional processes for making TiOPc Type I use 1-1-chloronaphthalene as a reaction solvent. Because 1-chloronaphthalene is a chlorinated solvent, the processes using 1-chloronaphthalene produce chlorinated waste. Such chlorinated waste is toxic and thus presents difficulties in disposal. In fact, 1-chloronaphthalene itself is toxic and presents safety handling issues. Due to these serious toxicity and safety issues associated with. 1-chloronaphthalene, it is no longer commercially available in North America. Thus, there is a need for a new solvent that has the desirable properties of 1-chloronaphthalene, such as a being chemically inert, and having a high boiling point, but without the toxicity. Most importantly the solvent has to be selective to produce TiOPc Type I in the synthesis and the TiOPc type I thus produced should convert to the high photosensitivity TiOPc Type IV crystal form with the desired photoactive properties. In addition, the solvent needs to be commercially available and economical.

BRIEF SUMMARY

According to embodiments illustrated herein, there is provided novel processes for making a pigment for use in electrophotographic applications that address the shortcomings discussed above.

In one embodiment, there is provided a process for synthesis of titanyl phthalocyanine using tetrahydronaphthalene as a reaction solvent.

In another embodiment, there is provided a process for synthesis of titanyl phthalocyanine, comprising: adding titanium alkoxide and 1,3-diiminoisoindoline to the tetrahydronaphthalene solvent to form a mixture, heating the mixture in order form titanyl phthalocyanine, cooling the mixture to precipitate titanyl phthalocyanine Type I, separating the titanyl phthalocyanine Type I, and subjecting the titanyl phthalocyanine Type I to a washing with hot N,N-dimethylformamide followed by a washing with hot dilute ammonia, hot water and warm methanol to produce a titanyl phthalocyanine Type I having a purity of at least 99 percent.

Yet another embodiment provides a process for synthesis of titanyl phthalocyanine, comprising adding titanium alkoxide, o-phthalodinitrile, and 1,3-diiminoisoindoline to the tetrahydronaphthalene solvent to form a mixture, heating the mixture in order form titanyl phthalocyanine, cooling the mixture to precipitate titanyl phthalocyanine Type I, separating the titanyl phthalocyanine Type I, and subjecting the titanyl phthalocyanine Type I to a washing with hot N,N-dimethylformamide followed by a washing with hot dilute ammonia, hot water and warm methanol to produce a titanyl phthalocyanine Type I having a purity of at least 99 percent.

BRIEF DESCRIPTION OF THE DRAWINGS

For a better understanding of the present embodiments, reference may be had to the accompanying figures.

DETAILED DESCRIPTION

Figure 1:
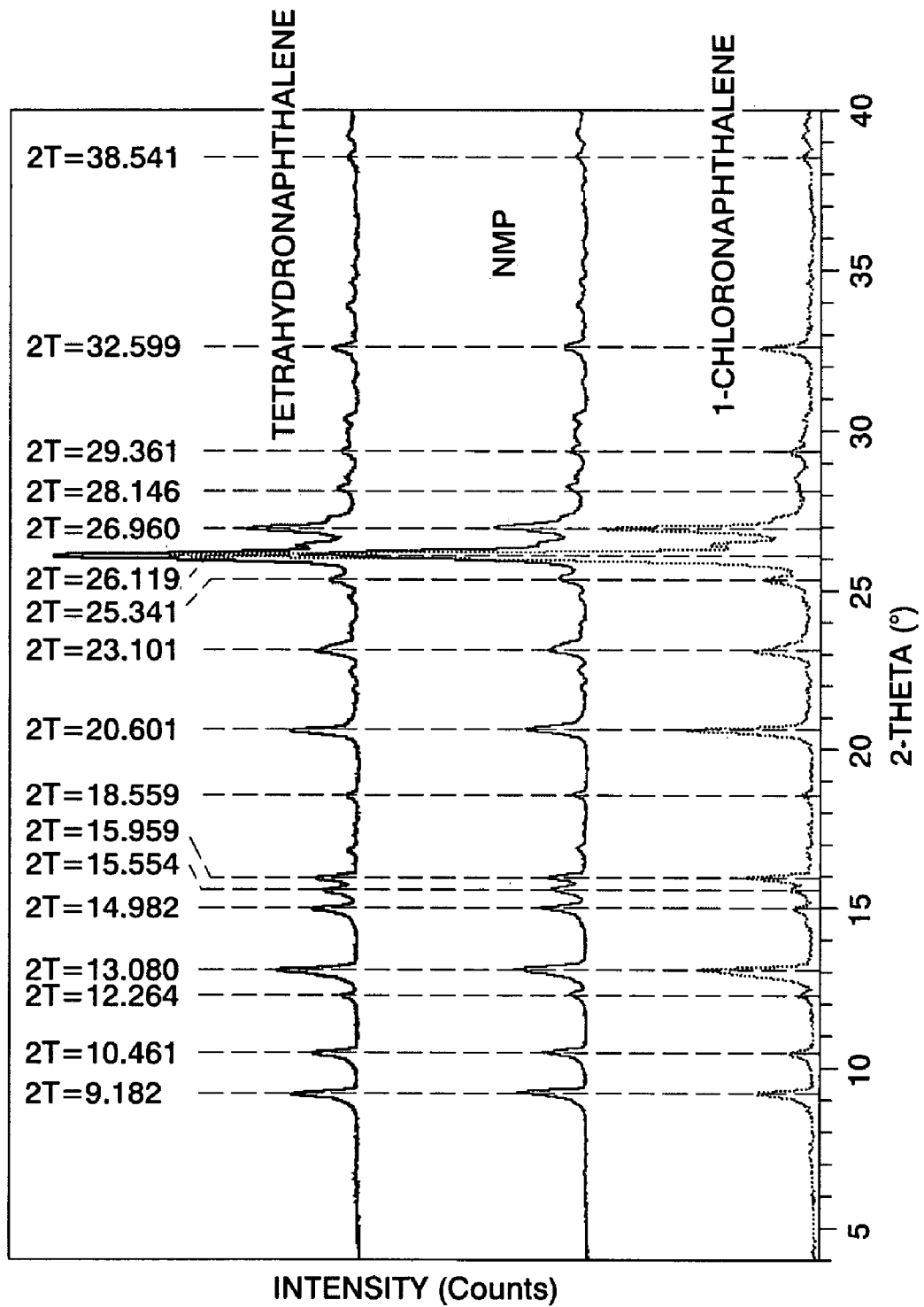
FIG. 1 is a XRD pattern of TiOPc Type I produced using tetrahydronaphtalene as a reaction solvent compared to TiOPc Type I using 1-chloronaphthalene and NMP as a reaction solvent.

It is understood that other embodiments may be utilized and structural and operational changes may be made without departure from the scope of the embodiments disclosed herein.

The embodiments relate to processes for making high yields of organic pigments, namely titanyl phthalocyanine (TiOPc) Type I, that is suitable to conversion to highly sensitive TiOPc Type IV for use in-the formulation of a charge generating layer. In embodiments, processes are described that produce good yields of TiOPc Type I with a solvent, novel in use with these described processes, which is commercially available, economical, and provides an environment-friendly alternative to conventionally used solvents.

There are existing processes known for synthesizing TiOPc Type I. One commonly used process involved the use of 1,3-diiminoisoindoline and a titanium alkoxide in 1-chloronaphthalene. As stated previously, 1-1-chloronaphthalene presents toxicity concerns and is no longer commercially available in North America. In addition, 1,3-diiminoisoindoline is an expensive intermediate that requires custom preparation, including purification steps. An alternative process used a mixture of o-phthalodinitrile and 1,3-diiminoisoindoline in n-methyl-2-pyrrolidone (NMP). The alternative was more economical because o-phthalodinitrile is significantly lower in cost as a raw material and by using both o-phthalodinitrile and 1,3-diiminoisoindoline, the amount of 1,3-diiminoisoindoline needed is reduced. While this process was more economical than the first process, it resulted in inferior TiOPc Type IV upon conversion.

Thus, the embodiments described herein present novel processes for preparing or synthesizing TiOPc Type I without the above problems. The processes can produce a titanyl phthalocyanine Type I having a purity of at least 99 percent. Three alternative solvents were evaluated for replacing 1-chloronaphthalene as a reaction solvent for reacting both 1,3-diiminoisoindoline with a titanium alkoxide as well as o-phthalodinitrile and 1,3-diiminoisoindoline with a titanium alkoxide: n-methyl-2-pyrrolidone (NMP) (bp=202° C.); decahydronaphthalene (bp=187° C.); and tetrahydronaphthalene (bp=207° C.). The evaluations demonstrated that tetrahydronaphthalene was the best alternative to 1-chloronaphthalene. Reaction in decahydronaphthalene resulted in a mixed Type I/Type II product which interfered with satisfactory conversion to the Type IV polymorph. In-addition, screening showed that, in a reaction using tetrahydronaphthalene as the solvent, the average yield of Type I pigment is significantly higher, for example by about 15%, compared to than one using NMP, in the 1,3-diiminoisoindoline route and the o-phthalodinitrile/1,3-diiminoisoindoline route.

The TiOPc Type I yield from the o-phthalodinitrile/1,3-diiminoisoindoline route in tetrahydronaphthalene is typically about 70% while the yield from the 1,3-diiminoisoindoline route in tetrahydronaphthalene is about 90%. The TiOPc Type I yield from o-phthalodinitrile/1,3-diiminoisoindoline route in NMP is typically about 60% while from the 1,3-diiminoisoindoline route in NMP is about 50%.

Figure 2:
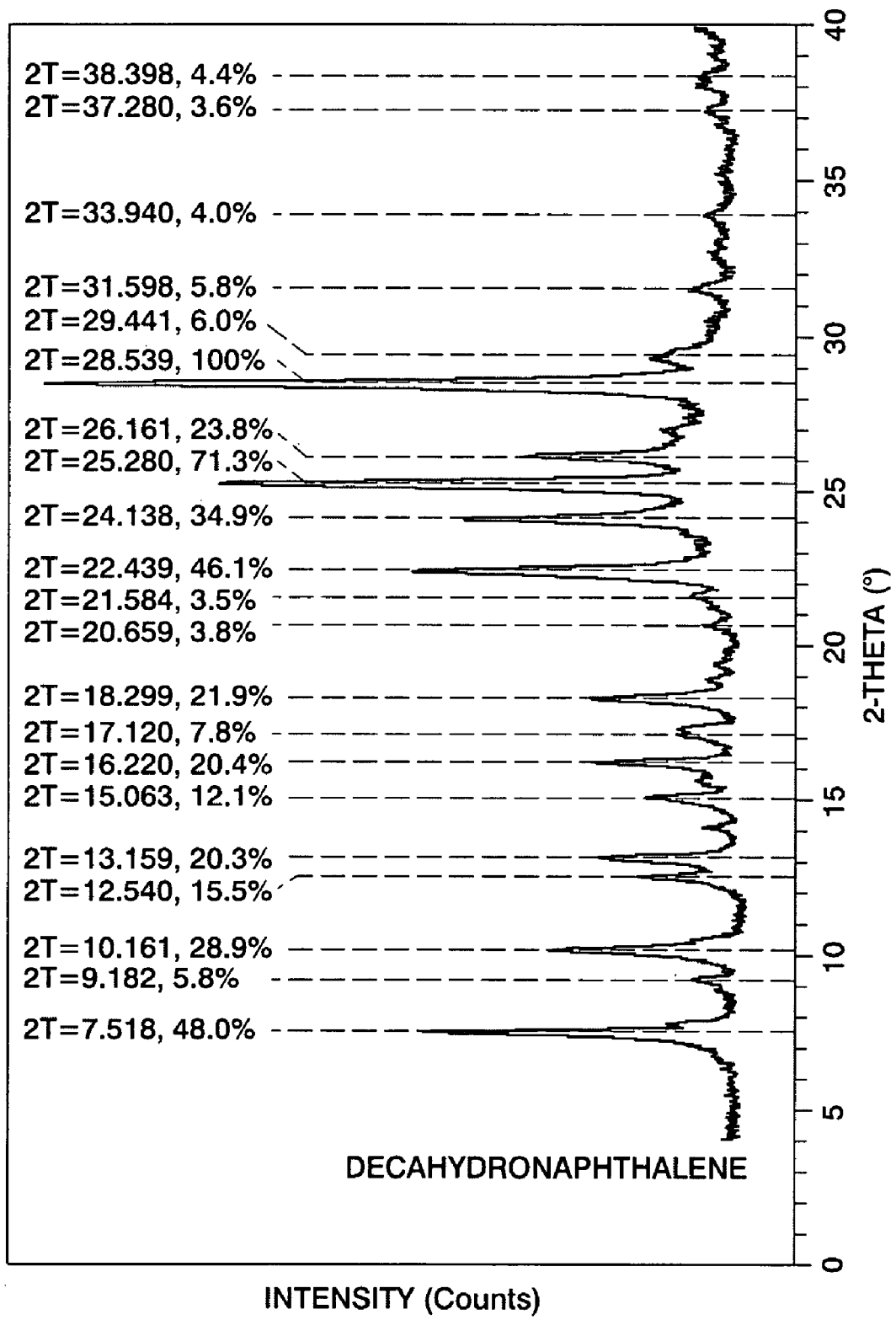
FIG. 2 is a XRD pattern of a mixed TiOPc-Type I/Type II produced using decahydronaphthalene as a reaction solvent.

The x-ray diffraction (XRD) pattern of the Type I polymorph obtained from reactions using tetrahydronaphthalene, NMP and 1-chloronaphthalene as solvents, are shown in FIG. 1. As can been seen, the characteristic major XRD Type I peaks are: 9.2, 13.1, 20.6, 26.1 and 27.0. In comparison, FIG. 2 shows the XRD pattern of a product obtained from a reaction using decahydronaphthalene as the solvent. A mixed Type-I/Type-II product results from the decahydronaphthalene synthesis, while both tetrahydronaphthalene and NMP synthesis produced the TiOPc Type I polymorph without the Type II impurity.

In the present embodiments, the processes may involve the following reactions:

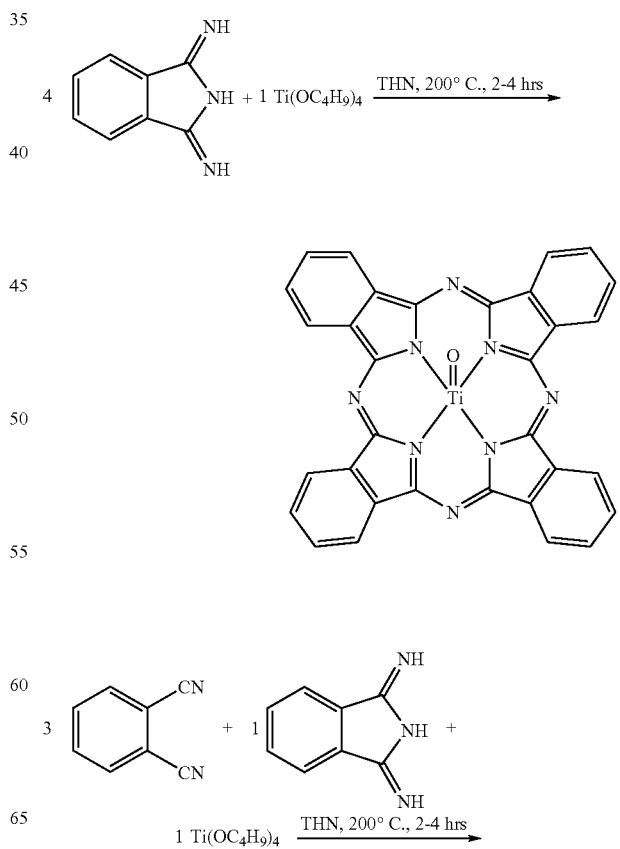

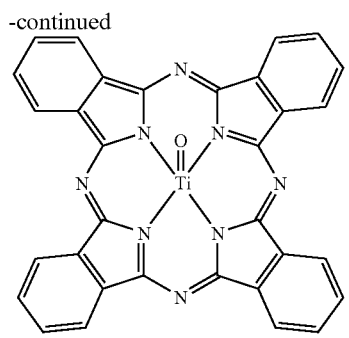

Ammonia and n-butanol are released as byproducts and titanyl phthalocyanine ($C_{40}H_{34}N_8O_2Ti$) Type I is produced. The TiOPc Type I may be further purified to the desired TiOPc Type I pigment by one or more washings. In some embodiments, the synthesis of the TiOPc Type I is followed by from about 1 to about 4 hot N,N-dimethylformamide (DMF) washes, from about 1 to about 2 hot ammonium hydroxide (4%) aqueous washes, a hot de-ionized water wash, and from about 1 to about 2 warm methanol washes. In a particular embodiment, the synthesis of the TiOPc Type I is followed by four boiling N,N-dimethylformamide (DMF) washes, two hot ammonium hydroxide (4%) aqueous washes, a hot de-ionized water wash, and two warm methanol washes.

In embodiments, the titanium alkoxide may be titanium-n-butoxide (TnBT) (available as TYZOR TnBT from DuPont (Wilmington, Del.)), titanium isopropoxide (available as TYZOR TPT from DuPont), tetraethyl titanate (available as TYZOR ET from DuPont), tetra-n-propyl titanate (available as TYZOR NPT from DuPont), tetra-2-ethylhexyl titanate (available as TYZOR TOT from DuPont), or mixtures thereof. In a particular embodiment, the reaction begins with reacting o-phthalodinitrile and 1,3-diiminoisoindoline in a 3:1 (mol/mol) ratio with titanium-n-butoxide in tetrahydronaphthalene for about 2 to about 4 hours at 200° C. In further embodiments, the reaction mixture of o-phthalodinitrile, 1,3-diiminoisoindoline and TnBT was slowly heated to improve the possible yield of the TiOPc Type I from the reaction using tetrahydronaphthalene (see examples). In one embodiment, the reaction mixture was slowly heated at a rate from about 1° C./min to about 3° C./min. Another embodiment involves using an excess of o-phthalodinitrile/1,3-diiminoisoindoline to titanium alkoxide to increase the yield. In an embodiment, the excess was from about 5% to about 50%.

In order to validate TiOPc Type I obtained from the reaction in tetrahydronaphthalene, a sample of TiOPc Type I was subjected to the standard polymorphic conversion procedure, consisting of an the acid pasting to the Type X polymorph, followed by conversion from the Type X polymorph to the Type IV polymorph (high sensitivity polymorph) through further purification. For example, the Type X polymorph may be converted to the Type IV polymorph by treating the Type X polymorph with chlorobenzene. The results, shown in Example 4 below, demonstrate that all samples of TiOPc Type I obtained from the reaction in tetrahydronaphthalene converted satisfactorily to the desired Type IV pigment with superior photoactive properties.

Thus, the present embodiments provide an improved chemical process which consistently produces TiOPc Type I in higher yields and without the use of any toxic solvent.

In general embodiments, the titanyl phthalocyanine Type IV pigment made through the processes described above is used as a photosensitive pigment in an imaging member (single layer) comprising a substrate, a charge generating layer disposed on the substrate, and at least one charge transport layer disposed on the charge generating layer. The Type IV pigment is used for the charge generating layer, and may be used alone or in combination with another pigment, such as metal phthalocyanines, metal free phthalocyanines, perylenes, hydroxygallium phthalocyanines, chlorogallium phthalocyanines, methoxygallium phthalocyanines, vanadyl phthalocyanines, selenium, selenium alloys, trigonal selenium, and the like, and mixtures thereof.

It will be appreciated that various of the above-disclosed and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

EXAMPLES

The examples set forth herein below and are illustrative of different compositions and conditions that can be used in practicing the present embodiments. All proportions are by weight unless otherwise indicated. It will be apparent, however, that the present embodiments can be practiced with many types of compositions and can have many different uses in accordance with the disclosure above and as pointed out hereinafter.

Example 1

Synthesis of Type I Titanyl Phthalocyanine in tetrahydronaphthalene via 1,3-diiminoisoindoline/TnBT Route 1-L stainless steel Buchi reactor equipped with single P4/45 impeller and hot oil bath circulator was charged with 300 g of tetrahydronaphthalene followed by 59.8 g of 1,3-diiminoisoindoline and 35 g of titanium tetrabutoxide. Reactor was purged with nitrogen and heated up to 200° C. at 2° C./min rate under 600 RPM stirring. Reactor contents color was changed from yellow to green to dark blue as the temperature increased as observed in the reactor sight glass. Reactor was held for 2 hrs at 200° C. then cooled to 90° C. and the reactor contents were discharged via bottom valve into the 15 cm diameter Buchner funnel and filtered on hot under vacuum. The product was washed four times with 70° C. dimethylformamide, followed by two 70° C. 4% aqueous ammonia washes followed by 70° C. deionized water wash and two 35° C. methanol washes. After drying under full vacuum at 70° C. overnight 46.7 g of product was recorded which represented 79% of the theoretical yield. The product was found to be Type I titanium phthalocyanine by XRD. The final sample showed the following elemental analysis results: C/H/N/O=66.3/2.9/18.8/2.3 respectively vs. theoretical 66.7/2.8/19.4/2.8 as well as $TiO_2$ content of 13.7% vs. 13.8% theoretical.

Example 2

Synthesis of Type I Titanyl Phthalocyanine in tetrahydronaphthalene via o-phthalodinitre/1,3-diiminoisoindoline/TPT Route 1-L stainless steel Buchi reactor equipped with single P4/45 impeller and hot oil bath circulator was charged with 300 g of tetrahydronaphthalene followed by 39.6 g of o-phthalodinitre, 14.9 g of 1,3-diiminoisoindoline and 29.2 g of titanium tetraisopropoxide (TYZOR TPT). Reactor was purged with nitrogen and heated up to 200° C. at 2° C./min rate under 400 RPM stirring. Reactor contents color was changed from yellow to green to dark blue as the temperature increased as observed in the reactor sight glass. Reactor was held for 2 hrs at 200° C. then cooled to 90° C. and the reactor contents were discharged via bottom valve into the 15 cm diameter Buchner funnel and filtered on hot under vacuum. The product was washed four times with 70° C. dimethylformamide, followed by two 70° C. 4% aqueous ammonia washes followed by 70° C. diionized water wash and two 35° C. methanol washes. After drying under full vacuum at 70° C. overnight 35.3 g of product was recorded which represented 60% of the theoretical yield. The product was found to be Type I titanium phthalocyanine by XRD.

Example 3

Synthesis of Type I Titanyl Phthalocyanine in tetrahydronaphthalene via o-phthalodinitre/1,3-diiminoisoindoline/TnBT and Slow Heating 2-L stainless steel Buchi reactor equipped with single P4/45 impeller and hot oil bath circulator was charged with 800 g of tetrahydronaphthalene followed by 105.6 g of o-phthalodinitre, 39.7 g of 1,3-diiminoisoindoline and 93.3 g of titanium-n-butoxide. Reactor was purged with nitrogen and heated up to 200° C. at 1° C./min rate under 400 RPM stirring. Reactor contents color was changed from yellow to green to dark blue as the temperature increased as observed in the reactor sight glass. Reactor was held for 2 hrs at 200° C. then cooled to 90° C. and the reactor contents were discharged via bottom valve into the 18 cm diameter Buchner funnel and filtered on hot under vacuum. The product was washed four times with 70° C. dimethylformamide, followed by two 70° C. 4% aqueous ammonia washes followed by 70° C. diionized water wash and two 35° C. methanol washes. After drying under full vacuum at 70° C. overnight 111.4 g of product was recorded which represented 71% of the theoretical yield. The product was found to be Type I titanium phthalocyanine by XRD.

Example 4

Synthesis of Type I Titanyl Phthalocyanine in tetrahydronaphthalene via excess (o-phthalodinitre/1,3-diiminoisoindoline)/TnBT and Slow Heating 2-L stainless steel Buchi reactor equipped with single P4/45 impeller and hot oil bath circulator was charged with 800 g of tetrahydronaphthalene followed by 115.8 g of o-phthalodinitre, 43.7 g of 1,3-diiminoisoindoline and 93.3 g of titanium-n-butoxide. Reactor was purged with nitrogen and heated up to 200° C. at 1° C./min rate under 400 RPM stirring. Reactor contents color was changed from yellow to green to dark blue as the temperature increased as observed in the reactor sight glass. Reactor was held for 2 hrs at 200° C. then cooled to 90° C. and the reactor contents were discharged via bottom valve into the 18 cm diameter Buchner funnel and filtered on hot under vacuum. The product was washed four times with 70° C. dimethylformamide, followed by two 70° C. 4% aqueous ammonia washes followed by 70° C. diionized water wash and two 35° C. methanol washes. After drying under full vacuum at 70° C. overnight 158 g of product was recorded which represented 79% of the theoretical yield. The product was found to be Type I titanium phthalocyanine by XRD.

In order to validate TiOPc Type I obtained from the reaction in tetrahydronaphthalene, samples of TiOPc Type I were subjected to the standard polymorphic conversion procedure, consisting of an acid pasting to the Type X polymorph, followed by conversion from the Type X polymorph to the Type IV polymorph (high sensitivity polymorph).

In each trial, a sample of TiOPc Type I, obtained from the tetrahydronaphthalene process, was dissolved in a mixture of 4/1 (vol/vol) methylene chloride/trifluoroacetic acid (TFA), and precipitated in a 10-fold excess of 1/1 (vol/vol) methanol/methylene chloride, followed by filtration and washing. Washing was done first with MeOH, then with hot and cold de-ionized water. The produced polymorph is designated as Type X. Type X is then converted to high sensitivity polymorph Type IV by stirring and treating the Type X polymorph with monochlorobenzene for about 1.5 hours, followed by dilution with MeOH, filtration and washing with MeOH.

Four TiOPc Type IV samples were subjected to electrical evaluation, with the results shown in Table 1. The evaluation was conducted under the following conditions: charge generator layer formulation: 60:40 pigment (TiOPc type IV): poly(vinyl butyral) (BMS) in n-butyl acetate; charge transport layer formulation 40:60 N,N'-diphenyl-N,N-bis(3-methyl phenyl)-1,1'-biphenyl-4,4'-diamine: polycarbonate Z in monochlorobenzene; testing conditions: E=−32 V/µm; Expose$_\lambda$=780 nm; Erase$_\lambda$=600-850 nm (200-250 ergs/cm$^2$). The Control TiOPc Type IV is a previously made reference sample from TiOPc Type I made with 1-chloronaphthalene as solvent. The sample R1-C11F was made as new reference sample from TiOPc Type I made with 1-chloronaphthalene as solvent, while the sample R1-C12F was made from TiOPc Type I made with tetrahydronaphthalene as solvent using 1,3-diiminoisoindoline, and the sample R1-C13F was made from TiOPc Type I made with tetrahydronaphthalene as solvent using 1,3-diiminoisoindoline and o-phthalodinitrile.

TABLE 1

Results of electrical evaluation of TiOPc Type IV made from TiOPc Type I (tetrahydronaphthalene route).

| Sample ID | Dark Decay (500 ms) (V) | $E_{1/2}$ (ergs/cm$^2$) | $E_{7/8}$ (ergs/cm$^2$) |
| --- | --- | --- | --- |
| Control | 5 | 1.11 | 2.88 |
| Pigment C11F | 3 | 1.14 | 2.97 |
| Pigment C12F | 5 | 1.22 | 3.11 |
| Pigment C13F | 3 | 1.18 | 3.08 |

All of the TiOPc Type I pigments were converted to TiOPc Type IV pigments. The two samples made from tetrahydronaphthalene show comparable dark decay and sensitivity as compared to the samples made in 1-chloronaphthalene. The results demonstrate that all samples of TiOPc Type I obtained from the reaction in tetrahydronaphthalene converted satisfactorily to the desired high sensitivity Type IV pigment. The results of Table 1 show that the reproducibility of the conversion of Type IV from Type I was achieved. In addition, the results confirm that conversion to Type IV from Type I, using a Type I synthesized using tetrahydronaphthalene solvent via 1,3-diiminoisoindoline route and the Type I synthesized using tetrahydronaphthalene solvent via o-phthalodinitre/1,3-diiminoisoindoline route, showed comparable electrical results to the Control.

All the patents and applications referred to herein are hereby specifically, and totally incorporated herein by reference in their entirety in the instant specification.

It will be appreciated that various of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims. Unless specifically recited in a claim, steps or components of claims should not be implied or imported from the specification or any other claims as to any particular order, number, position, size, shape, angle, color, or material.

What is claimed is:

1. A process for synthesis of titanyl phthalocyanine comprising:
   (a) providing tetrahydronaphthalene as a reaction solvent;
   (b) adding titanium alkoxide and 1,3-diiminoisoindoline to the tetrahydronaphthalene solvent to form a mixture;
   (c) heating the mixture in order form titanyl phthalocyanine;
   (d) cooling the mixture to precipitate titanyl phthalocyanine Type I; and
   (e) separating the titanyl phthalocyanine Type I.

2. The process of claim 1, wherein the titanyl phthalocyanine is obtained in a crystal form of titanyl phthalocyanine Type I.

3. The process of claim 1 further including
   subjecting the titanyl phthalocyanine Type I to a washing with hot N, N-dimethylformamide followed by a washing with hot dilute ammonia, hot water and warm methanol to produce a titanyl phthalocyanine Type I having a purity of at least 99 percent.

4. The process of claim 3 further including converting the titanyl phthalocyanine Type I to a high sensitivity crystal form titanyl phthalocyanine Type IV comprising the steps of
   (a) dissolving the titanyl phthalocyanine Type I in a mixture of a haloacetic acid and alkylene halide;
   (b) precipitating the titanyl phthalocyanine Type I to titanyl phthalocyanine Type X by adding the solution to a non-solvent mixture, the non-solvent mixture comprising one or more organic solvents;
   (c) filtrating and washing the titanyl phthalocyanine Type X;
   (d) stirring and treating the Type X polymorph with monochlorobenzene to produce titanyl phthalocyanine Type IV.

5. A process for synthesis of titanyl phthalocyanine comprising:
   (a) providing tetrahydronaphthalene as a reaction solvent;
   (b) adding titanium alkoxide and a mixture of 1,3-diiminoisoindoline and o-phthalodinitrile to the tetrahydronaphthalene solvent to form a mixture;
   (c) heating the mixture in order form titanyl phthalocyanine;
   (d) cooling the mixture to precipitate titanyl phthalocyanine Type I;
   (e) separating the titanyl phthalocyanine Type I;
   (f) subjecting the titanyl phthalocyanine Type I to a washing with hot N, N-dimethylformamide followed by a washing with hot dilute ammonia, hot water and warm methanol to produce a titanyl phthalocyanine Type I having a purity of at least 99 percent.

6. The proces of claim 5, wherein an excess of the o-phthalodinitrile and 1,3-diiminoisoindoline to the titanium alkoxide is used to increase a yield of the titanyl phthalocyanine Type I pigment.

7. The process of claim 6, wherein the excess is from about 5% to about 50%.

8. The process of claim 5, wherein the o-phthalodinitrile, the 1,3-diiminoisoindoline, the titanium alkoxide, and the tetrahydronaphthalene are slowly heated to increase a yield of the titanyl phthalocyanine Type I pigment.

9. The process of claim 8, wherein the o-phthalodinitrile, the 1,3-diiminoisoindoline, the titanium alkoxide, and the tetrahydronaphthalene are slowly heated at a rate of from about 1° C./min to about 3° C./min.

* * * * *